United States Patent [19]

Valli

[11] Patent Number: 4,644,950
[45] Date of Patent: Feb. 24, 1987

[54] HIGH FREQUENCY RESECTION ENDOSCOPE WITH MOVEMENT ACTUATED SWITCH

[75] Inventor: Bruno Valli, Perugia, Italy

[73] Assignee: Olympus Winter & Ibe, GmbH, Hamburg, Fed. Rep. of Germany

[21] Appl. No.: 711,162

[22] Filed: Mar. 13, 1985

[30] Foreign Application Priority Data

Mar. 17, 1984 [DE] Fed. Rep. of Germany ....... 3409944

[51] Int. Cl.⁴ ............................................ A61B 17/39
[52] U.S. Cl. ................................................ 128/303.15
[58] Field of Search ........... 128/303.1, 303.13, 303.15; 200/61.58, 61.73, 61.85, 153 A, 153 T

[56] References Cited

U.S. PATENT DOCUMENTS

| 2,545,865 | 3/1951 | Wallace | 128/303.15 |
| 4,030,502 | 6/1977 | Iglesias | 128/303.15 |
| 4,041,952 | 8/1977 | Morrison et al. | 200/61.58 |
| 4,060,086 | 11/1977 | Storz | 128/303.15 |
| 4,174,714 | 11/1979 | Mehl | 128/303.13 |
| 4,274,070 | 6/1981 | Thiene | 128/303.13 |
| 4,274,413 | 6/1981 | Hahn et al. | 128/303.13 |
| 4,430,996 | 2/1984 | Bonnet | 128/303.15 |
| 4,540,871 | 9/1985 | Corrigall et al. | 200/61.85 |

Primary Examiner—Edward M. Coven
Assistant Examiner—Max F. Hindenburg
Attorney, Agent, or Firm—Walter C. Farley

[57] ABSTRACT

A resection endoscope has a high frequency energized cutting electrode which can be moved longitudinally by a carrier. A switch for the high frequency current is mounted on the carrier so that when the carrier is actuated in the cutting direction the current is switched on and is otherwise switched off. Thus the switch actuation is coupled to the carrier actuation for simplifying the operation. A certain lost motion is advantageously provided for the switch actuation which enables the high frequency current to be selectively switched on or off even when the cutting electrode is stationary.

10 Claims, 5 Drawing Figures

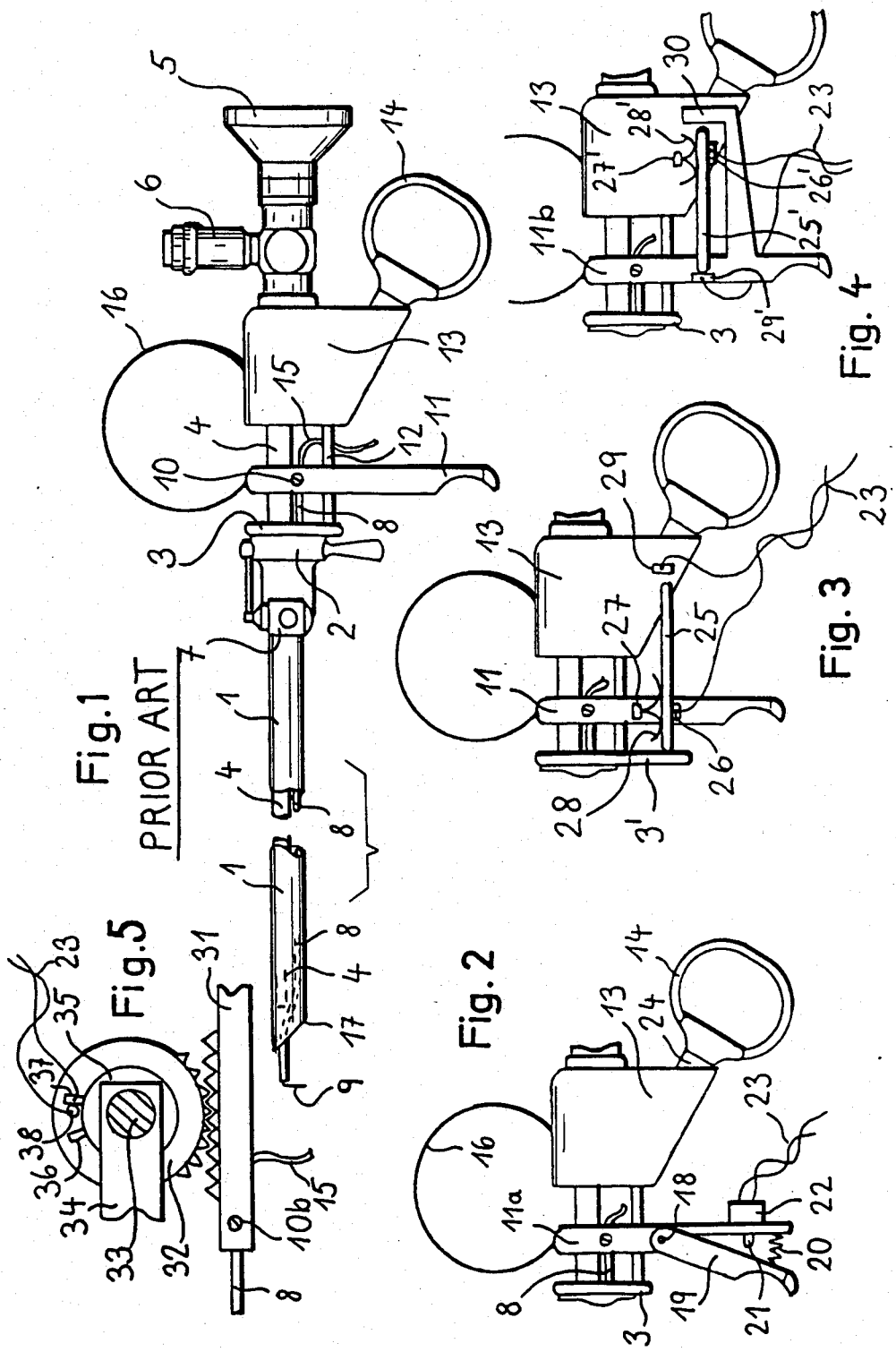

HIGH FREQUENCY RESECTION ENDOSCOPE WITH MOVEMENT ACTUATED SWITCH

This invention relates to a resection endoscope of the type having a hollow shaft, a high frequency cutting electrode longitudinally movable in the shaft and carrier means for supporting and moving the electrode, the resectoscope having improved power control means for supplying high frequency energy to the cutting electrode.

BACKGROUND OF THE INVENTION

In resection endoscope with a high frequency-energized cutting electrode, the electrode is commonly moved in the longitudinal direction of the instrument by means of an actuating mechanism on the endoscope structure into the desired cutting position and, particularly in a urological resectoscope, is drawn in a particular direction during the cutting process. A high frequency power generator is connected to the electrode through a switch by which the operator can control the supply of high frequency current. The current can be switched directly or by indirect control of the HF generator. Commonly, the switch is constructed as a foot switch positioned within the reach of the operator.

Many different structural forms of carriers and actuators are known for such instruments, but commonly two handles are arranged to be mutually movable in the longitudinal direction of the instrument, one being moved with the thumb and the other with the index finger. In most cases, the movement occurs in one direction against the force of a spring and automatically, with the aid of the spring, in the other direction. However, carriers or actuators which are moved by different structures such as by means of a rack and pinion drive can be used.

One known resectoscope of the type generally referred to above has the HF switch on the carrier. In this construction, the switch is arranged so that it is operated with a different finger independently of the operation of the actuating device.

A disadvantage of the known resection endoscopes is the fact that the actuation of that portion of the carrier which causes movement of the electrode and the actuation of the power switch are accomplished independently and, thus, twice as much attention is required from the operator in order to properly synchronize the carrier actuation and the switch actuation in a desired manner so that the switch is closed only during actuation of the carrier in the cutting direction. As will be recognized, the term "closed" refers to a switch condition in which the power circuit is complete, allowing current to flow to the electrode. Incorrect operation can occur for various reasons such as the result of a shock or startled reaction to unforeseen events or simply as the result of inattention. Such incorrect operation can lead, for example, to moving the cutting electrode in the wrong direction with the HF current switched on. This can result in serious injuries to the patient.

SUMMARY OF THE INVENTION

An objective of the present invention is to provide a resection endoscope in which the demands made on the attention of the operator are reduced and the operating safety of the instrument is thereby increased.

A further object is to provide an endoscope in which the energization of the cutting electrode is accomplished as the result of movement control of the electrode without requiring separate activity on the part of the operator.

Briefly described, the invention comprises a resection endoscope of the type having an elongated, hollow shaft, a high frequency cutting electrode longitudinally and movably disposed in the shaft and carrier means for supporting the shaft and for moving the electrode longitudinally relative to the shaft for resection. The improvement comprises circuit means connectable to a source of high frequency power for supplying energizing current to the electrode and switch means mounted on the carrier means for selectively closing the circuit means or activiating the power supply. The carrier means includes actuating means for moving the electrode and for closing the switch means when the electrode is moved in its cutting direction.

BRIEF DESCRIPTION OF THE DRAWINGS

In order to impart full understanding of the manner in which these and other objectives are attained inaccordance with the invention, particularly advantageous embodiments thereof will be described with reference to the accompanying drawings, which form a part of this specification, and wherein:

FIG. 1 is a side elevation, in partly schematic form, of a conventional urological resectoscope;

FIG. 2 is a partial side elevation of a resectoscope similar to FIG. 1 incorporating a first embodiment of switch means in accordance with the invention;

FIGS. 3 and 4 are partial side elevation similar to FIG. 2, showing respectively second and third embodiments of switch means in accordance with the invention; and FIG. 5 is a partial side elevation of a rack and pinion actuation means showing a further embodiment of switch means in accordance with the invention.

DESCRIPTION OF THE PREFERRED EMBODIMENTS:

A urological resection endoscope or resectoscope of conventional construction is shown in FIG. 1 in side elevation in order to explain the operation of the carrier structure and, in particular, the actuation devices with which the apparatus of the present invention are used.

An endoscope shaft 1 is fixedly and removably connected by means of a coupling structure 2 to a base plate 3 of the carrier. An optical tube 4 extends along the entire length of the resectoscope and is provided at the proximal end with an eyepiece 5 and a light conductor connection 6 for admitting light so that the procedures can be monitored visually. It is also customary to provide a water connection tap 7 to admit water on the shaft in the vicinity of coupling 2.

A rod-like, insulated supply conductor 8 extends along the interior of shaft 1. Conductor 8 is longitudinally movable within shaft 1 and has, at its distal end, a high frequency cutting end of conductor 8 passes through base plate 3 and is surrounded by a sealing connection, the portion of conductor 8 extending to the proximal side of base plate 3 being actuated for movement of the loop in the longitudinal direction of shaft 1.

The proximal end of conductor 8 is fixedly attached by a clamping screw 10 to a movable handle 11 which is mounted on the carrier. Handle 11 is supported and guided for longitudinal movement on optical tube 4 and on a parallel guide rod 12. A fixed handle 13, which is fixedly mounted relative to base plate 3, is provided with a thumb ring 14 of conventional construction.

Feed conductor 8 is connected by a conductor 15 to a high frequency power generator, not shown. The other terminal of the generator in a conventional way is connected to a ground plate at the patient, high frequency current flowing from cutting loop 9 through patient tissue between the terminals of the generator. A switch, now shown, which is conventionally constructed as a foot switch, is provided for the purpose of switching the high frequency current either by directly breaking or completing the high frequency circuit, e.g. breaking conductor 15, or by suitable control of the generator.

When the instrument of FIG. 1 is actuated, the carrier is grasped with one hand so that the thumb passes throught the gripping ring 14 and the operator's index finger engages movable handle 11, conveniently resting in the recess near the bottom of the handle. By pulling the index finger relative to the thumb, handle 11 is moved in the proximal direction (to the right in FIG. 1) and the feed conductor 8 and the cutting loop 9 are accordingly moved to the right, withdrawing the cutting loop into shaft 1. By moving the movable handle 11 in the opposite direction, the cutting loop 9 is moved in the distal direction. Conventionally, however, a leaf spring 16 is provided as illustrated in the drawing between the two handles so that cutting loop 9 is automatically moved in the distal direction, this motion being stopped or reversed by the withdrawing force of the operator's index finger.

When the cutting loop is withdrawn into the tube, one can cut tissue by, in conventional operation technology, trapping tissue between the cutting loop and the lower edge 17 of the distal opening of shaft 1 in a manner somewhat similar to a scissor action. Depending upon the desires and requirements of the operator, cutting can also be accomplished in the reverse direction or with the electrode stationary relative to shaft 1. The carrier structure illustrated can be modified in many ways. For example, the two mutually movable handles can be constructed in the manner of a pair of scissors or operated with a rotary drive in which the cutting loop movement is actuated by a rack and pinion arrangement.

When operating the instrument, the operator must take care that he switches on the high frequency current by means of, for example, the conventional foot switch, during the desired cutting process, that is to say, commonly during the withdrawing (proximal) movement of the cutting loop 9 but leaves the power switched off otherwise in order not to cause undesired injuries to the patient by chance contact. He must therefore concentrate on the correct operation of the carrier by optical monitoring through the eyepiece 5 and also on the correct operation of the high frequency switch.

The present invention will now be described with reference to FIGS. 2-5, FIGS. 2-4 showing specific embodiments of the invention as applied to a resectoscope having a movement actuation system similar to FIG. 1 and FIG. 5 having a different form of carrier actuation. Those parts of the instrument which remain the same are designated with like reference numerals in the various figures.

In the embodiment of FIG. 2 a lever 19 is pivotally mounted at 18 on the movable handle 11a, lever 19 being movable toward and away from the main portion of handle 11a and being urged toward the open position by a spring 20. When lever 19 is moved toward the lower portion of handle 11a portion 19 contacts an operating member 21 of a switch 22. Switch 22 is a normally open switch connected via conductors 23 to a HF generator so as to selectively supplying HF current to cutting loop 9.

The apparatus shown in FIG. 2 is operated using the thumb and index finger as in the known construction of FIG. 1. When the operator released handle 11a for the purpose of permitting the cutting loop 9 to move in the distal direction, the switch 22 is not actuated and the current is switched off. When handle 11a is operated to move the cutting loop in the proximal direction, movable portion 19 is swung toward the main portion of handle 11a in the initial part of the movement, first operating switch 22 and then moving the cutting loop 9. thus, in this embodiment, the high frequency power is always switched on when the loop is being withdrawn and always switched off during outward or forward movement. The switching on and off of the HF current thus occurs automatically. The operator need not concentrate on correct switching on and off of the power apart from his control over the movement of the cutting loop.

As will be seen in FIG. 2, a small, predetermined amount of lost motion or "play" is provided between lever 19 and the switch actuating member 21 in the spread apart position. This results in increased safety and, additionally, permits the possibility of stopping the forward or outward movement of the cutting loop with only light pressure on lever 19 without switching on the HF current. Only when the handle is pulled back further is the current switched on. If the spring 20 which urges the handle portion apart and the leaf spring 16 urging the handle and loop assembly forward are appropriately selected then the operator, with the cutting loop being stationary, can both switch on the high frequency current by gently pulling on the finger or switch it off by gently relieving the pressure of the finger. In this manner, it is possible to cut even when the cutting loop is stationary. This can be employed, for example, for stopping bleeding by coagulation or cauterizing or for similar processes.

In a variation of the embodiment of FIG. 2, a switch of similar construction as is provided on handle 11a could, alternatively, be provided on the fixed portion 13 of the structure by providing for movement of the thumb ring 14 so that the switch is actuated in a functionally similar manner by thumb pressure, i.e., by pulling the two handles 11a, 13 together.

In a simplified embodiment, it is also possible to omit lever 19 to permit the switch operator 21 to be actuaged directly by the index finger.

A different form of switch structure is shown in FIG. 3, illustrated again in the context of a resection endoscope of the type shown in FIG. 1. This switch construction includes a switching rod 25 which is slidably mounted on movable handle 11 with its longitudinal axis generally parallel with the direction of movement of the resection device, i.e., generally parallel with optical tube 4 and guide rod 12. Rod 25 is positioned on a sliding contact 26 which is fixedly mounted on the side of handle 11 and is held against contact 26 by a pair of engagement springs 28 supported in a block 27. Springs 28 thus hold the rod against contact 26 so that the rod can be slidably moved in the direction of its longitudinal axis and parallel to the actuation direction of the carrier structure. End abutments are provided at opposite ends of the switching rod, one abutment being formed by a contact member 29 fixedly attached to stationary handle 13 in the proximal direction. The other abutment is formed by base plate 3' in the distal direction. Sliding contact 26 and contact member 29 are made of electrically conducted material, contact 29 being contected to one of the wires 23 leading to the HF power source. Rod 25 is also made of an electrically conductive material. Contact member 26 is connected to the other of the wires 23 being connected to the HF power source. The base plate 3' is made of an insulating material, at least in the region of contact with rod 25, as are all other components of the carrier which could come into contact with the switching rod. The switching arrangement is illustrated as being of open construction. However, in a practical embodiment, the switching components are provided with an insulated housing shielding the switching arrangement on all sides.

In the switch position illustrated in FIG. 3, rod 25 is in abutment with base plate 3'. The switch is open in this position so that the HF current is not being supplied to loop 9. If handle 11 is moved further forward, then the sliding mounting including contact 26 and springs 28 slides along the rod. If the movable handle 11 is then withdrawn (moved to the right) to perform a cutting opeation, the rod is carried along in the proximal direction and abuts contact member 29. This completes the circuit between conductors 23 energizing the loop with the HF current. If the movable handle 11 is further withdrawn, the sliding mounting 26, 28 slides along the rod while maintaining electrical contact and completion of the electrical circuit. If the movable handle 11 is moved forward again the circuit is promptly opened.

A degree of lost motion is provided in this arrangement also. The function is basically the same as described in connection with the embodiment of FIG. 2. The construction illustrated in FIG. 3 is characterized by considerable simplicity, sturdiness and reliability and can be used to switch very large quantities of power directly, particularly of the high frequency current.

In FIG. 4 a modification of FIG. 3 is illustrated in which the switch of FIG. 3 is provided in kinematic reversal. As shown in FIG. 4 a switching rod 25' is provided in a corresponding sliding mount 26', 28' which is supported on the stationary handle 13. An electrically conductive end contact 29', which is connected to a conductor from cable 8, is provided on the movable handle 11b. An electrically insulated end abutment 30 is fixedly attached to and movable with handle 11b. A predetermined amount of lost motion is again provided by the length of the arm supporting abutment 30 as compared with the length of rod 25'. The mode of operation is identical to that of the embodiment of FIG. 3. A protective housing should again be provided in a practical embodiment of the apparatus.

FIG. 5 shows an embodiment usable with a rotationally actuated carrier which operates somewhat similarly regarding the electrical switching processes for the HF current. The movable portions of the carrier can be provided on an instrument of the type shown in FIG. 1. A conductor 8 carrying cutting loop 9 is driven by a rack 31 which is longitudinally movably mounted with respect to the stationary portions of the carrier, i.e., relative to base plate 3 and handle 13. Rack 31 is driven by pinion 32 which is rotatably mounted on a shaft 33. Shaft 33 is journaled in a member 34 fixedly attached to the carrier structure.

A switching wheel 35 is also mounted on shaft 33 and is provided with two radially extending abutment pegs 36 and 37 which are circularly spaced apart, wheel 35 being attached to and rotatable with the shaft which is rotated by the operator by manually turning a hand knob, not illustrated for the sake of simplicity. A carrier peg 38 protrudes laterally from the side of pinion 32 and extends between pegs 36 and 37. Peg 38 and abutment peg 37 are electrically conductive, peg 38 being connected to one of the wires 23 leading to HF power source and peg 37 being connected to the other wire 23.

When shaft 33 is rotated by the operator the pinion 32 is carried with it in one or the other direction by virtue of engagement with the one or the other of abutment pegs 36, 37 against peg 38. Thus, cutting loop 9 is moved in either the distal or proximal direction. If the movement occurs in the distal direction, peg 38 engages insulating abutment peg 36. The switch thus remains open. If movement occurs in the opposite direction in which it is intended to operate in the cutting mode, peg 38 engages electrically conductive abutment 37 and the circuit is closed, delivering HF current to the cutting loop. Abutments 36, 37 are spaced such that a predetermined degree of lost motion is again provided. The function as regards the coupling of the switch actuation and movement of the cutting loop 9 is again in accordance with that explained in connection with FIG. 2.

A switch in accordance with the invention for rotary actuated carriers can be differently constructed in an analogous manner leading to many modifications which are possible depending on the construction parameters. In the illustrated embodiments it is always assumed that cutting movement is in the proximal, i.e., withdrawing direction. If the switching function is reversed one can also cut in the distal direction. This depends upon which cutting direction is preferred by the operator.

As will be seen, in accordance with the invention the actuation of the carrier in the cutting direction is compulsorily coupled to the actuation of the switch. Thus, the HF current is only switched on when the apparatus is actuated in the cutting direction. As soon as movement in the other direction is initiated the current is switched off. The operator need no longer concentrate on switching the HF current but only the correct movement of the carrier whereupon the current is automatically switched in the correct manner. Thus, the operation of an endoscope incorporating the present invention is greatly simplified and the operational safety increased.

Suitable switches can be provided, for instance, as pressure operated switches working without lost motion which are arranged on one of the mutually movable parts of the carrier on the respective abutment surface and switched when acted upon by pressure in the sense of the cutting direction. However, the lost motion features are advantageously provided. A small lost motion enables the switching on and off of the current when the carrier and, thus, the cutting electrode are stationary by a small actuating movement in one or the other direction. Thus, when the electrode is stationary it can be switched on or off at the choice of the operator. In addition to the automatic switching on of the current during the curring movement, cutting or cauterizing is thus also made possible when the electrode is stationary.

It is also advantageous to provide a handle with relatively movable parts as illustrated in FIG. 2. A structure with a switch provided on one of the handle portions can be provided relatively economically and in a structurally simple fashion.

It is also advantageous to use the highly durable and sturdy switch arrangement of FIGS. 3 and 4 which is particularly suitable for directly switching the HF current.

In the embodiments of the invention shown in the drawings 2 to 5 the switch means are connected by wires 23 to the HF power supply, not shown, to switch it on or off respectively. Thereby HF current is supplied selectively to supply conductor 8 and cutting loop 9. In an alternative obvious way the switch means shown in the drawings can be used to switch the HF current directly. In that case one of the wires 23 is connected to the HF output of the power supply, the other of the wires 23 being connected to the supply conductor 8.

As it is well known in this field of surgical technic, in a conventional way the cutting loop 9 is connected to one HF output terminal of the HF power generator. The other output terminal of the HF power generator is grounded and connected to the patient's body, e.g. by means of a ground plate being fixed to the patient's leg. The HF current therefore is flowing from cutting loop 9 through patient's body to the ground plate.

While certain advantageous embodiments have been chosen to illustrate the invention, it will be understood by those skilled in the art that various changes and modifications can be made therein without departing from the scope of the invention as defined in the appended claims.

What I claim:

1. A resection endoscope of the type having an elongated hollow shaft, a high frequency cutting electrode longitudinally and movably disposed in said shaft and carrier means for supporting said shaft and for moving said electrode longitudinally in a cutting direction relative to said shaft for resection wherein the improvement comprises circuit means connectable to a source of high frequency power for supplying energizing current to said electrode; and switch means mounted on said carrier means for selectively breaking said circuit means or actuating said power source, said carrier means including actuating means for moving said electrode and for simultaneously closing said switct means, said actuating means being operative to automatically close said switch means whenever said actuating means is operated to place said electrode in motion in it cutting direction independent of the actual position of the electrode.

2. An endoscope according to claim 1, wherein said actuating means is constructed so as to be movable a small, predetermined distance before closing said switch means.

3. An endoscope according to claim 2, wherein said carrier means includes a fixed handle secured to said shaft, said actuating means comprises a movable handle coupled to said electrode, and said switch means is mounted on one of said handles and has an operator member extending toward and contactable by the other one of said handles during motion thereof in the cutting direction.

4. An endoscope according to claim 3, wherein said switch means comprises an elongated rod slidably supported on said one of said handles with its longitudinal axis generally parallel with the direction of motion of said movable handle;

a first abutment member mounted on said other one of said handles aligned with said longitudinal axis of said rod so that said first abutment member is contacted by said rod after said handles have been moved toward each other, said rod and said first abutment member being electrically conductive and being connected to said circuit means or said power source; and a second abutment member aligned with said axis at the opposite end of said rod from said first member.

5. An endoscope according to claim 2, wherein said carrier means includes a fixed handle secured to said shaft, said actuating means comprises a movable handle having first and second relatively movable portions, and said switch means is mounted on one of said relatively movable portions and has an operator member extending toward and contactable by the other of said relatively movable portions.

6. An endoscope according to claim 2, wherein said actuating means includes first and second relatively movable portions and, wherein said switch means comprises an elongated rod slidably supported on said one of said relatively movable portions with its longitudinal axis generally parallel with the direction of motion of said portion;

a first abutment member mounted on said other one of said relatively movable portions aligned with said longitudinal axis of said rod so that said first abutment member is contacted by said rod after said portions have been moved toward each other, said rod and said first abutment member being electrically conductive and being connected to said circuit means; and a second abutment member aligned with said axis at the opposite end of said rod from said first member.

7. An endoscope according to claim 1, wherein said carrier means inlcudes a fixed handle secured to said shaft, said actuating means comprises a movable handle coupled to said electrode, and said switch means is mounted on one of said handles and has an operator member extending toward and contactable by the other one of said handles during motion thereof in the cutting direction.

8. An endoscope according to claim 1, wherein said carrier means includes a fixed handle secured to said shaft, said actuating means comprises a movable handle having first and second relatively movable portions, and said switch means is mounted on one of said relatively movable portions and has an operator member extending toward and contactable by the other of said relatively movable portions.

9. An endoscope according to claim 2 wherein said carrier means includes a fixed handle secured to said shaft, said actuating means comprises a movable handle coupled to said electrode and said switch means is mounted on a gripping surface of one of said handles to be operated by a gripping finger of the operator.

10. An endoscope according to claim 1 wherein said carrier means includes a fixed handle secured to said shaft, said actuating means comprises a movable handle coupled to said electrode and said switch means is mounted on a gripping surface of one of said handles to be operated by a gripping finger of the operator.

* * * * *